(12) United States Patent
Fukui

(10) Patent No.: US 9,084,741 B2
(45) Date of Patent: *Jul. 21, 2015

(54) GRANULAR JELLY BEVERAGE FOR MEDICATION AND PROCESS FOR PRODUCING THE SAME

(75) Inventor: Atsuko Fukui, Chiyoda-ku (JP)

(73) Assignee: RYUKAKUSAN CO., LTD., Tokyo (JP)

( * ) Notice: Subject to any disclaimer, the term of this patent is extended or adjusted under 35 U.S.C. 154(b) by 270 days.

This patent is subject to a terminal disclaimer.

(21) Appl. No.: 12/682,747

(22) PCT Filed: Oct. 12, 2007

(86) PCT No.: PCT/JP2007/069934
§ 371 (c)(1),
(2), (4) Date: Apr. 12, 2010

(87) PCT Pub. No.: WO2009/047859
PCT Pub. Date: Apr. 16, 2009

(65) Prior Publication Data
US 2010/0239684 A1 Sep. 23, 2010

(51) Int. Cl.
| A61K 9/16 | (2006.01) |
| A23L 1/05 | (2006.01) |
| A61K 36/00 | (2006.01) |
| A23L 1/00 | (2006.01) |
| A23L 1/22 | (2006.01) |
| A23L 2/38 | (2006.01) |
| A23L 2/52 | (2006.01) |
| A61K 9/00 | (2006.01) |

(52) U.S. Cl.
CPC .............. *A61K 36/00* (2013.01); *A23L 1/0017* (2013.01); *A23L 1/22083* (2013.01); *A23L 2/38* (2013.01); *A23L 2/52* (2013.01); *A61K 9/0095* (2013.01); *A23V 2002/00* (2013.01)

(58) Field of Classification Search
None
See application file for complete search history.

(56) References Cited

U.S. PATENT DOCUMENTS 5,576,039 A * 11/1996 Lewis ........................ 426/250
6,180,159 B1 * 1/2001 Villagran et al. ........... 426/590
6,277,395 B1 8/2001 Fukui et al.

FOREIGN PATENT DOCUMENTS

| JP | 04-346937 A | 12/1992 |
| JP | 07-115942 A | 5/1995 |
| JP | 09-194346 A | 7/1997 |
| JP | 11-124342 A | 5/1999 |
| JP | 11-322624 A | 11/1999 |
| JP | 2002-218917 A | 8/2002 |
| WO | 2005/025622 A1 | 3/2005 |

OTHER PUBLICATIONS

Machine translation of JP07-115942, original document published May 1995.*
D. J. W. Burns, et al., "Evaluation of the separate contributions of viscosity and sweetness of sucrose to perceived viscosity, sweetness and bitterness of vermouth", Journal of Texture Studies, 1985, pp. 365-381, vol. 16.
Rose Marie Pangborn, et al., "Effect of hydrocolloids on apparent viscosity and sensory properties of selected beverages", Journal of Texture Studies, 1978, pp. 415-436, vol. 9.

* cited by examiner

*Primary Examiner* — Nissa Westerberg
(74) *Attorney, Agent, or Firm* — Sughrue Mion, PLLC

(57) ABSTRACT

Provided is a granular jelly beverage for medication used for taking the crude drug(s) and/or herbal medicine(s), which granular jelly beverage for medication comprises (a) 0.1 to 15.0% by mass of a bitterness masking ingredient comprising a plant fat and oil and/or animal fat and oil; (b) 5.0 to 20.0% by mass of a bitterness masking auxiliary ingredient comprising a sugar alcohol; (c) 0.1 to 5.0% by mass of an aggregation-inhibiting gelling ingredient; (d) 0.1 to 5.0% by mass of at least one taste adjusting ingredient selected from the group consisting of acids, derivatives thereof and salts thereof; and (e) a balance of water.

11 Claims, 2 Drawing Sheets

GRANULAR JELLY BEVERAGE FOR MEDICATION AND PROCESS FOR PRODUCING THE SAME

CROSS REFERENCE TO RELATED APPLICATION

This application is a National Stage of International Application No. PCT/JP2007/069934 filed Oct. 12, 2007, the contents of which is incorporated herein by reference in its entirety.

FIELD OF THE INVENTION

The present invention relates to a granular jelly beverage for medication, which beverage enables tastes of drugs such as crude drugs or herbal medicines having a unique bitter taste, astringent taste, sour taste or sweet taste to be adjusted and allows the drugs to be safely taken, as well as a process for producing the granular jelly beverage for medication.

BACKGROUND ART

Conventionally, drugs for oral application are, in general, taken with water or plain boiled water. Yet, it is difficult for patients having difficulties in swallowing, in particular, the elderly, children and the like to take drugs with water or plain boiled water.

For the elderly, children and the like, the drug in a form of capsule, tablet or the like is ground and mixed into rice, miso soup or juice to be taken, which is laborious and complicated. In addition, such a way of taking the drug makes release time of drug ingredients uncontrollable, inevitably leading to impairment of pharmacological effects and chemical reactions. Also, it becomes unfeasible to mask the tastes. In some cases, the intended pharmacological effects may not be attained.

The present applicants proposed a low calorie, non-sugar swallowing-assisting beverage, which beverage has a prescribed jelly strength and contains thickening agents such as agar and carrageenan, mannitol and to make the taking of the drug easier while retaining the intended pharmacological effects. A patent has been granted on this beverage (See Patent Literature 1).

Further, the present applicants improved the above-mentioned swallowing-assisting beverage and proposed a bitterness masking granular jelly beverage enabling bitterness to be masked even in drugs containing a basic substance with a nitrogen atom such as an amino group (See Patent Literature 2).

Patent Literature 1: Japanese Patent No. 3257983
Patent Literature 2: WO 2005/025622

Meanwhile, drugs such as crude drugs and herbal medicines are, in general, available mostly in the form of granules. Since each granule has, in many cases, low specific gravity, when the herbal medicine is put in the mouth together with water, the granule herbal medicine with powdery or gritty feel floats on the surface of the water, which makes the swallowing with water difficult. In addition, for crude drugs and herbal medicines, a large dose per one application also causes difficulties in the swallowing with the water in the mouth.

In order to facilitate the swallowing of these crude drugs and herbal medicines, it is thought, for example, to use the above-mentioned bitterness masking granular jelly beverage.

Yet, crude drugs and herbal medicines have a unique astringent taste, sour taste or sweet taste in addition to bitterness. Because of this, there are some cases where those drugs do not have a harmonized taste with the above-mentioned bitterness masking granular jelly beverage which contains animal fats and oils and/or plant fats and oils. Consequently, some may rather find more difficult to take the drug.

To improve the taste of the granular jelly beverage after the mixing with the drug, it can be thought, for example, to add an acidulant or the like to the granular jelly beverage. However, the simple addition of the acidulant causes aggregation of ingredients constituting the granular jelly beverage and disables appropriate gel formation. Thus, there is a case where the jelly is not formed suitably for coating the drug.

DISCLOSURE OF THE INVENTION

The present invention was made in light of the above-described problems in the prior art. An object of the present invention is to provide a granular jelly beverage for medication, which beverage is able to mask bitterness of a drug without its pharmacological effects being lost and to coat the drug such that the drug is readily swallowed, and has a good taste even after mixed with the drug, even when the drug is a crude drug and/or herbal medicine which has the bitterness as well as a unique astringent taste, sour taste or sweet taste.

As a result of intensive studies for attaining the above-described object, the present inventor found that use of a beverage containing a bitterness masking ingredient and at least one taste adjusting ingredient selected from the group consisting of acids, derivatives thereof and salts thereof, together with one containing an aggregation-inhibiting gelling ingredient, is able to solve the above-mentioned problems, thereby completing the present invention.

Accordingly, the granular jelly beverage for medication according to the present invention is a granular jelly beverage for medication used for taking a crude drug(s) and/or herbal medicine(s), which granular jelly beverage for medication comprises:

(a) 0.1 to 15.0% by mass of a bitterness masking ingredient comprising a plant fat and oil and/or animal fat and oil;

(b) 5.0 to 20.0% by mass of a bitterness masking auxiliary ingredient comprising a sugar alcohol;

(c) 0.1 to 5.0% by mass of at least one type of an aggregation-inhibiting gelling ingredient selected from the group consisting of carrageenan, gellan gum, locust bean gum, xanthane gum, guar gum, pectin, tapioca starch, and starch;

(d) 0.1 to 5.0% by mass of at least one type of a taste adjusting ingredient selected from the group consisting of acids, derivatives thereof and salts thereof; and (e) a balance of water.

Also, the method for producing the granular jelly beverage for medication according to the present invention is a method comprising mixing the bitterness masking ingredient (a), the bitterness masking auxiliary ingredient (b), the aggregation-inhibiting gelling ingredient (c) and at least a part of the water (e) to obtain a mixture; and thereafter mixing the taste adjusting ingredient (d) into the mixture to produce the granular jelly beverage for medication.

BEST MODE FOR CARRYING OUT THE INVENTION

Figure 1:
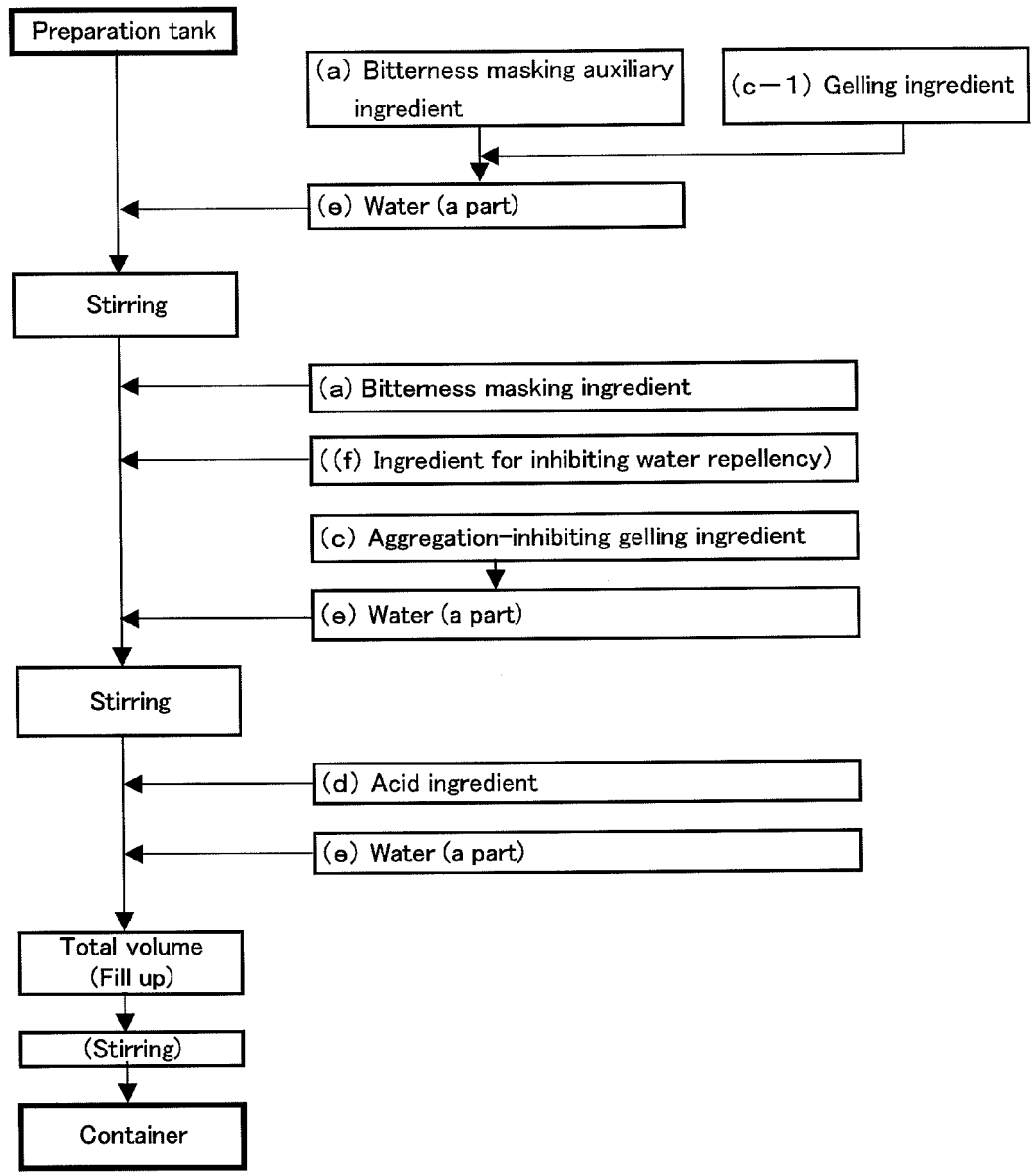
FIG. 1 is a flow diagram showing an example of the steps of producing the granular jelly beverage for medication according to the present invention.

The molded article of the present invention will be described in detail below. Unless otherwise specified, "%" used herein means percentage by mass.

As described above, the granular jelly beverage for medication according to the present invention facilitates the taking of crude drug(s) and/or herbal medicine(s), and comprises (a) 0.1 to 15.0% by mass of the bitterness masking ingredient comprising a plant fat and oil and/or animal fat and oil; (b) 5.0 to 20.0% by mass of the bitterness masking auxiliary ingredient comprising a sugar alcohol; (c) 0.1 to 5.0% by mass of the aggregation-inhibiting gelling ingredient; (d) 0.1 to 5.0% by mass of at least one taste adjusting ingredient selected from the group consisting of acids, derivatives thereof and salts thereof; (e) a balance of water; and, as necessary, (f) 0.01 to 1.5% by mass of the ingredient for inhibiting water repellency.

[(a) Bitterness Masking Ingredients]

The bitterness masking ingredient of the granular jelly beverage for medication according to the present invention is at least either plant fats and oils or animal fats and oils. These bind to receptors present on human taste bud, which receptors sense bitterness, and function to block binding of bitter ingredients of the drug and the like to these receptors.

That is, in human, tastes of food and the like are perceived by taste receptor organs called the taste buds present near the surface of the tongue. This taste bud measures about 50 μm in diameter. There are taste cells inside the tongue and the receptors sensing bitter tastes, sour tastes, salty tastes or umami tastes are located on the surface of the plasma membrane. And, when bitter substances of the drug which is mixed with saliva to be an aqueous solution bind to the bitter taste receptors, an electric potential difference between the inside and outside of the plasma membrane of the taste cells is altered. Then, this electric potential difference is transmitted to the cerebral cortex via nerve fibers. Bitterness is thereby perceived.

In the present invention, the bitterness masking ingredient binds to the bitter taste receptors prior to binding of the bitter ingredients to the receptors, covers the bitter taste receptors and blocks the binding between the bitter ingredients and bitter taste receptors, thereby inhibiting the excitement of the taste cells and preventing the occurrence of the electric potential difference.

The above-mentioned animal fats and oils or plant fats and oils are not restricted as long as those fats and oils fulfill the above-mentioned functions. Examples of the plant fats and oils include cacao fats and oils, lecithin, soybean oil, salad oil, edible safflower oil, sunflower oil, canola oil, corn oil, rice bran oil, peanut oil, olive oil, sesame oil, linseed oil, coconut oil, palm oil, mixed oil, margarine or shortening, and any mixture of these. And, examples of the animal fats and oils include lard, unsalted butter, butter, cheese, cream, meat fats, fish oils and any mixture of these.

Among these animal fats and oils or plant fats and oils, unsalted butter, butter, soybean oil, lecithin, olive oil, corn oil and cacao oil are preferred with cacao fats and oils being most preferred.

Milk, soy milk or extracted components of these, besides the above-mentioned animal fats and oils or plant fats and oils, may be used.

The content of the bitterness masking ingredient in the granular jelly beverage for medication according to the present invention is 0.10 to 15.0%, more preferably 0.20 to 13.0%, still more preferably 0.25 to 11.0%.

In cases where the content is less than 0.1%, sufficient bitterness masking effects cannot be attained whereas the physical property of the jelly is altered and thus a proper jelly strength cannot be obtained in cases where the content is more than 15.0%.

[(b) Bitterness Masking Auxiliary Ingredients]

The bitterness masking auxiliary ingredient (b) of the granular jelly beverage for medication according to the present invention is a sugar alcohol. Since this acts as a sweetener, it has auxiliary effects in bitterness masking. Further, the sugar alcohol has a function of improving the stability of the gel.

The sugar alcohols are not restricted and examples thereof include hydrogenated maltose starch syrup, hydrogenated starch syrup, hydrogenated lactose, xylitol, erythritol, sorbitol, mannitol and any mixture of these. Among these sugar alcohols, erythritol, hydrogenated maltose starch syrup, hydrogenated starch syrup, xylitol and sorbitol are preferred.

The content of the bitterness masking auxiliary ingredient in the granular jelly beverage for medication according to the present invention is 5.0 to 20.0%, preferably 6.0 to 18.0%, more preferably 8.0 to 16.0%.

In cases where the content is less than 5.0%, sufficient bitterness masking auxiliary effects cannot be attained. An addition exceeding 20.0% makes the effects saturated and results in no significant difference.

[(c) Aggregation-Inhibiting Gelling Ingredients]

In the present description, the term "aggregation-inhibiting gelling ingredient" refers to those not only inhibiting aggregation of the granular jelly beverage for medication but also functioning as a gelling agent when the granular jelly beverage for medication is acidic.

The pH of a conventional bitterness masking granular jelly beverage is in a neutral pH range between 5 and 8 such that the beverage coats a drug containing a basic substance which intramolecularly contains a nitrogen atom derived from an amino group or the like, facilitates the taking of the drug, and suppresses perception of bitter taste caused by drug dissolution in the mouth (See Japanese Patent Application No. 2003-321623).

Meanwhile, since an aqueous solution dissolving crude drugs and/or the herbal medicines containing crude drugs is generally acidic, such drugs do not have a harmonized taste with the bitterness masking granular jelly beverage having a neutral pH range of 5 to 8. Thus, the palatability deteriorates and some may rather find difficulties in swallowing the drugs. In addition, there are some cases where pharmacological effects of the herbal medicine are inhibited.

For instance, a simple addition of an acidulant to the above-mentioned granular jelly beverage such that the beverage has a harmonized taste with the herbal medicines and the like may result in an aggregation by a deceased solubility of bitterness masking ingredient, gelling ingredient and the like into the beverage, or a chemical reaction, as well as no formation of gels. Therefore, a preferred mode of the granular jelly for coating the drug may not be attained.

In view of this, by including the aggregation-inhibiting gelling ingredient (c) in conjunction with the bitterness masking ingredient (a), the bitterness masking auxiliary ingredient (b) and the taste adjusting ingredient (d), the present invention improves the taste of the granular jelly beverage for medication without the occurrence of an aggregation between the bitterness masking ingredient and the taste adjusting ingredient, and enables the granular jelly beverage to have a jelly physical property of appropriate solidity and to coat the herbal medicine or the like, which facilitates the swallowing of even herbal medicines requiring a large dose or the like.

As the aggregation-inhibiting gelling ingredient which also functions as the gelling ingredient, at least one selected from the group consisting of carrageenan, gellan gum, locust bean gum, xanthane gum, guar gum, pectin, tapioca starch and starch can preferably be used.

The content of the aggregation-inhibiting gelling ingredient in the granular jelly beverage for medication according to the present invention is 0.1 to 5.0%, preferably 0.1 to 4.0%, more preferably 0.1 to 3.0%.

In cases where the content is less than 0.1%, a jelly strength of not less than 10 g/cm$^2$ cannot be attained whereas, in cases where it is more than 5.0%, suitable granules are not formed, leading to the physical property unsuitable for taking a crude drug, herbal medicine or the like.

[(c-1) Gelling Ingredients]

The granular jelly beverage for medication according to the present invention may further contain the gelling ingredient (c-1) in addition to the above-mentioned aggregation-inhibiting gelling ingredient.

As the gelling ingredient (c-1) of the granular jelly beverage for medication according to the present invention, agar, furcellaran, gelatin, curdlan, psyllium seed gum, alginic acid, alginate, mannan, tamarind gum, dextran, carboxymethyl cellulose, carboxymethyl cellulose sodium or any mixture of these can be used in combination.

The content of the aggregation-inhibiting gelling ingredient in the total amount of the aggregation-inhibiting gelling ingredient (c) and the gelling ingredient (c-1) is preferably 2.0 to 100.0%, more preferably 5.0 to 95.0%, still more preferably 10.0 to 90.0%.

When the content of the aggregation-inhibiting gelling ingredient in the total amount of the aggregation-inhibiting gelling ingredient (c) and the gelling ingredient (c-1) is less than 2.0%, a little aggregation may occur after addition of the taste adjusting ingredient, which is not preferred.

[(d) Taste Adjusting Ingredients]

The granular jelly beverage for medication according to the present invention further contains at least one taste adjusting ingredient selected from the group consisting of acids, derivatives thereof and salts thereof. In cases where the pH of the granular jelly beverage for medication is in an acidic range, the taste does not deteriorate and the palatability can be improved when mixed with crude drugs, herbal medicines or the like which have a light sour taste. Because of this, the use of the granular jelly beverage for medication according to the present invention enables the drug such as the herbal medicine to be readily swallowed even in the case of a large dose.

The taste adjusting ingredient is preferably at least one selected from the group consisting of adipic acid, L-ascorbic acid, L-asparatic acid, L-arginine, L-glutamic acid, citric acid, glucono delta lactone, gluconic acid, succinic acid, DL-tartaric acid, L-tartaric acid, lactic acid, fumaric acid, butyric acid, DL-malic acid, derivatives thereof and salts thereof.

Concrete examples thereof include adipic acid, L-ascorbic acid, L-ascorbic acid salts, L-ascorbic acid esters, derivatives of L-ascorbic acid, L-asparatic acid, L-arginine, L-glutamic acid salts, citric acid, citric acid salts, glucono delta lactone, gluconic acid, gluconic acid salts, succinic acid, succinic acid salts, DL-tartaric acid, L-tartaric acid, lactic acid, lactic acid salts, fumaric acid, fumaric acid salts, butyric acid, derivatives of butyric acid, DL-malic acid and DL-malic acid salts.

Among these acids, derivatives thereof and salts thereof, citric acid, L-ascorbic acid and DL-malic acid are preferred.

The content of the taste adjusting ingredient in the granular jelly beverage for medication according to the present invention is 0.1 to 5.0%, preferably 0.1 to 4.0%, more preferably 0.15 to 4.0%.

In cases where the content is less than 0.1%, the taste of the granular jelly beverage for medication cannot be modified so as to have a harmonized taste with crude drugs, herbal medicines or the like. In cases where the content is more than 5.0%, no effects to improve the taste are expected when the granular jelly beverage for medication is mixed with herbal medicines or the like, and, in addition, an aggregation is likely to occur, which is not preferred.

[(e) Water]

The granular jelly beverage for medication according to the present invention contains water. Any water suitable for drinking is sufficient and, for example, tap water, various types of ion-exchanged water, purified water or the like can be used.

The content of the water is not restricted. As long as it is an amount remaining from the amount of other ingredients other than water, in other words, as long as the total amount of each ingredient and water is 100%, any amount may be employed.

[(f) Ingredients for Inhibiting Water Repellency]

The granular jelly beverage for medication according to the present invention can further contain the ingredient for inhibiting water repellency (f) as necessary.

The ingredient for inhibiting water repellency exerts a function to improve the blending with water by inhibiting the water repellency of the above-mentioned bitterness masking ingredient. Additionally, in cases where the bitter ingredients described later have poor water solubility such as lipid solubility, or in cases where a wax coating or polymer coating is performed during the formulation, the ingredient for inhibiting water repellency has an action of enhancing the affinity between those bitter ingredients or the coating and jelly, as well as making the coating function more effective.

Concrete examples of such an ingredient for inhibiting water repellency include sucrose fatty acid esters, glycerin fatty acid esters, sorbitan fatty acid esters, propylene glycols, propylene glycol fatty acid esters and any mixture of these.

The content of the ingredient for inhibiting water repellency is preferably 0.01 to 1.5%, more preferably 0.02 to 1.4%, still more preferably 0.03 to 1.3%.

When the content is less than 0.01% sufficient effects for inhibiting the water repellency may not be attained. A further addition exceeding 1.5% makes the effects saturated and may, in some cases, may result in no significant differences.

As long as the granular jelly beverage for medication exerts the masking effect, the effect to assist the swallowing, and the effect to improve the taste, all of which effects are intended by the present invention, it can contain, besides the above-mentioned essential ingredients, gelling promoting agents, saccharides which are nutrient sources, sweeteners and other additives including flavoring agents.

For instance, as the gelling promoting agent, calcium lactate can be added to 0.1 to 2.0%.

The granular jelly beverage for medication according to the present invention, which beverage is composed of the above-mentioned ingredients does not suppress an intrinsic natural sweet or sour taste of a crude drug, herbal medicine or the like. It rather has effects to make these tastes stand out and to improve the overall taste. This facilitates the taking of crude drug, herbal medicine or the like which has a unique bitter taste, astringent taste, sour taste or sweet taste. Thus, it can preferably be used particularly when children or the like take a crude drug, herbal medicine or the like.

Next, properties of the granular jelly beverage for medication according to the present invention will be described.

This jelly beverage has circumferentially water or the like and is an aggregate of granular jellies whose shape is uniform or not uniform. The pH thereof is preferably 2.5 to 5.0, more preferably 2.7 to 4.5, particularly preferably 3.0 to 4.0.

In cases where the pH is less than 2.5, a sour taste stands out and bitter and astringent tastes of a crude drug or herbal medicine are strongly perceived. In cases where the pH is more than 5.0, the sour and astringent tastes of a crude drug or herbal medicine are strongly perceived and the palatability deteriorates, which are not preferred.

Also, the jelly strength at 20° C. is preferably 10 to 100 $g/cm^2$, more preferably 20 to 80 $g/cm^2$, still more preferably 20 to 70 $g/cm^2$.

In cases where the jelly strength is less than 10 $g/cm^2$, it cannot be said that there are no possibilities to cause troubles such as aspiration for those who have difficulty in swallowing. In cases where the jelly strength is more than 100 $g/cm^2$, the granular jelly may be too hard to be smoothly swallowed.

Also, the maximum length of the granular jelly, that is, when a line segment across granular jelly's inside is assumed in the granular jelly usually having a shape of pillar, cone or oval sphere, the length of the longest line segment is preferably 1 to 10 mm, more preferably 1 to 8 mm.

In cases where the maximum length of the granular jelly is less than 1 mm, the granular jelly is rendered very close to a form of paste and may adhere to and remain in the throat. In cases where the maximum length is more than 10 mm, the granular jelly may clog the throat and its adhesion with the drug such as the herbal medicine may possibly deteriorate.

Since the granular jelly beverage for medication according to the present invention has the above-mentioned shape and jelly strength, it coats herbal medicine or the like in the form of granule or powder with low specific gravity in the granular jelly beverage and the granular jelly beverage does not separate from the drug in the mouth. Because of this, by using the granular jelly for medication according to the present invention, even a crude drug and/or herbal medicine in the form of granule or powder which readily adhere to the throat does not remain in the mouth or the throat. And, healthy subjects and patients in frail health or suffering from various diseases, who find difficulties in swallowing the drug, can readily take a relatively large dose of the herbal medicine.

Further, since the granular jelly beverage for medication according to the present invention can firmly coat the drug, it is suitable for taking a large dose of crude drug, herbal medicine, or the like. For example, 2 to 3 g of granules of the drug is firmly coated in 20 ml of the granular jelly beverage for medication according to the present invention, which allows this drug to be easily taken.

For example, in the case of a granular herbal medicine, a dose per one application is usually about 2 to 3 g.

With a granular jelly having its maximum length of 1 to 10 mm, granules which are widely used as a formulation of herbal medicine can be readily coated.

Furthermore, although the granular jelly beverage for medication according to the present invention has the coating function as described above, it is mainly composed of water. Also, when it is warmed to near body temperature (about 37° C.), the jelly strength decreases and the coating function is lost. Thus, there are no effect on the disintegration and dissolution property of the drug. Since there are also no interaction between the granular jelly beverage and the drug, pharmacological effects of crude drugs or herbal medicines are not impaired.

Since the granular jelly beverage for medication is a non-sugar beverage, it is suitable for diabetic patients. Also, since the beverage is unlikely to cause a cavity even when taken immediately before going to bed, it is suitable for children. Further, since the beverage goes through a sterilization step, it can be safely used by patients with weak physical strength, decreased resistance, or compromised immunity, as well as children.

Examples of a drug which facilitates the swallowing when taken with granular jelly beverage for medication according to the present invention include drugs using herbal medicine prescriptions or crude drugs (Korean ginseng, various herbs or the like) which have been approved by the Ministry of Health, Labour and Welfare.

Examples of the type of formulation include solid formulations such as powders, granules, balls, capsules, powdered extracts or tablets and liquid formulations such as extracts or syrups.

Next, an example of a method for producing the granular jelly beverage for medication according to the present invention will now be described referring to the drawings. It should be noted that the method for producing the granular jelly beverage for medication is not limited to the method described below.

FIG. 1 is a flow diagram showing an example of an embodiment of the method for producing the granular jelly beverage for medication according to the present invention.

As shown in FIG. 1, the bitterness masking auxiliary ingredient (b) and the aggregation-inhibiting gelling ingredient (c) or the gelling ingredient (c-1) are first subjected to powder mixing and then the resulting powder mixture is fed into warmed water (at not less than about 50° C.) and stirred for a prescribed time to obtain a substantially uniform mixture. Next, the bitterness masking ingredient (a) is fed and as necessary the ingredient for inhibiting water repellency (f) is fed. After the resulting mixture is mixed for a prescribed time, the aggregation-inhibiting gelling ingredient (c) is further fed and stirred to obtain a substantially uniform mixture. Thereafter, to the obtained mixture, the taste adjusting ingredient (d) is fed and as necessary, the flavoring agent or the like is added. And then, the whole mixture is adjusted (filled up) with water (e). The resultant is filled in a container and is as necessary, subjected to sterilization, cooling and the like, thereby obtaining the granular jelly beverage for medication.

In cases where the aggregation-inhibiting gelling ingredient (c) and/or the gelling ingredient (c-1) is/are added separately in twice dividedly into 2 portions, the aggregation-inhibiting gelling ingredient (c) may be first added and then the gelling ingredient (c-1) may be added. These ingredients may be added in the reverse order. Or, the aggregation-inhibiting gelling ingredient (c) may be added twice.

When the solution is stirred and mixed, it is preferred that the solution be warmed to 50 to 100° C., more preferably to 70 to 100° C. while being stirred and mixed.

Figure 2:
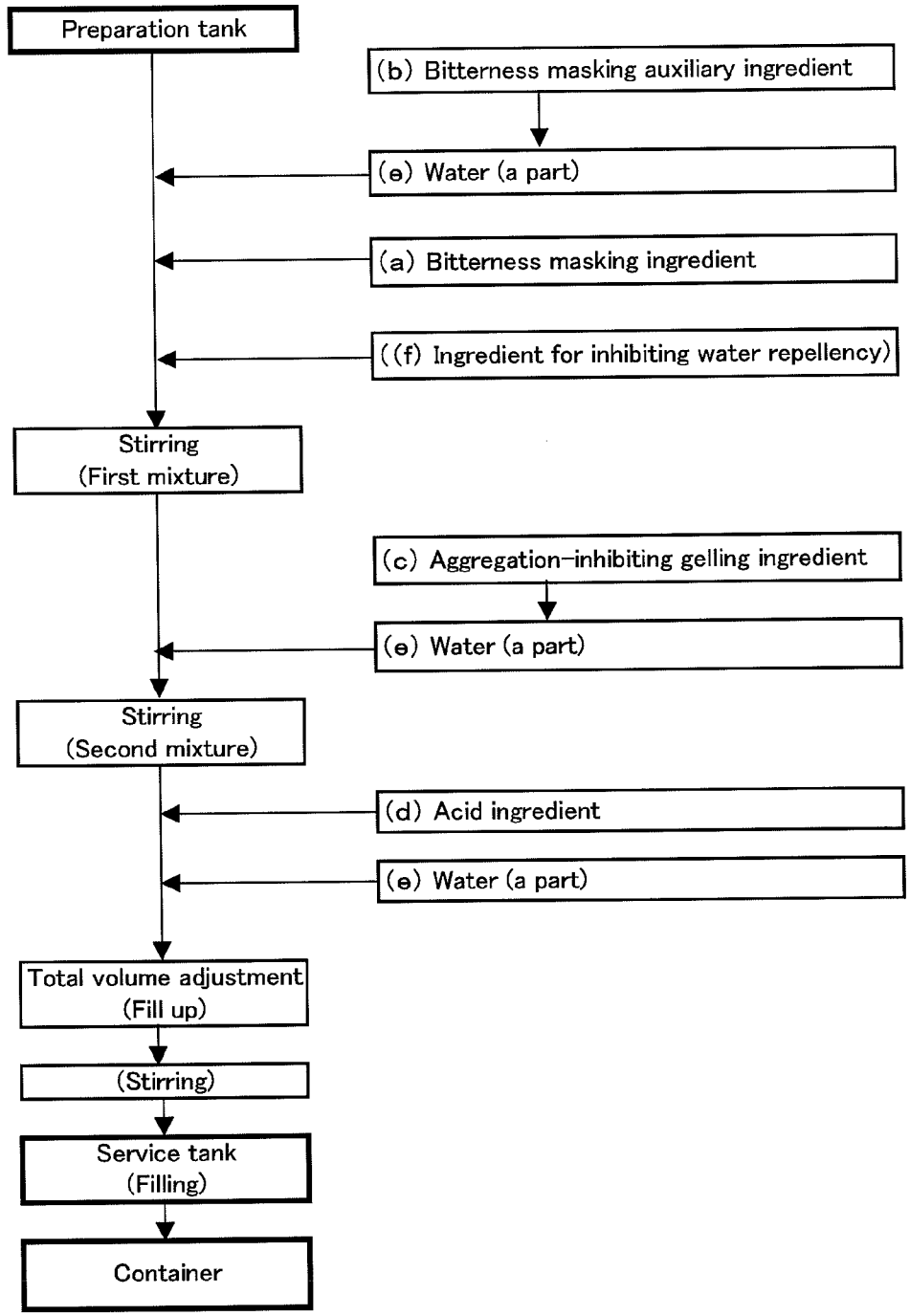
FIG. 2 is a flow diagram showing another example of the steps of producing the granular jelly beverage for medication according to the present invention

FIG. 2 is a flow diagram showing another example of an embodiment of the method for producing the granular jelly beverage for medication according to the present invention. In the method for production in this example, the bitterness masking auxiliary ingredient (b) is first fed into water warmed to not less than about 50° C. and stirred for a prescribed time to substantially uniformly mix the resultant. Next, the bitterness masking ingredient (a) is fed and as necessary, the ingredient for inhibiting water repellency (f) is fed. The resulting mixture is stirred for a prescribed time, thereby obtaining a mixture (first mixture). Further, the aggregation-inhibiting gelling ingredient (c) mixed in advance with water warmed to not lower than 50° C. is fed into the first mixture and stirred, thereby obtaining a substantially uniform mixture (second mixture). Thereafter, to the obtained second mixture, the taste adjusting ingredient (d) is fed and as necessary, the flavoring agent or the like is added. And then, the whole mixture is adjusted (filled up) with water (e). The resulting mixture is filled in a container and as necessary subjected to sterilization, cooling or the like, thereby obtaining the granular jelly beverage for medication.

As shown in FIG. 2, the aggregation-inhibiting gelling ingredient (c) and the gelling ingredient (c-1) may be added in a preparation tank at once, not separately.

The order of mixing the bitterness masking ingredient (a), the bitterness masking auxiliary ingredient (b), aggregation-inhibiting gelling ingredient (c) and at least a part of water (e) is not restricted. To the mixture obtained by mixing these (a, b, c and e), the taste adjusting ingredient (d) may be added and mixed.

In the method for producing the granular jelly beverage for medication, the bitterness masking ingredient (a), the bitterness masking auxiliary ingredient (b), aggregation-inhibiting gelling ingredient (c) and at least a part of water (e) are substantially uniformly mixed to obtain a mixture and thereafter, the taste adjusting ingredient (d) is added to the mixture. By doing so, aggregation or the like is unlikely to occur in the granular jelly beverage and thus the granular jelly beverage having a preferred mode for coating crude drug, herbal medicine or the like can be produced.

The granular jelly beverage for medication can preferably be used when a drug such as crude drug, herbal medicine or the like having a bitter taste as well as sour taste is taken. As a way of taking such a drug, for example, the drug such as crude drug, herbal medicine or the like is first put in the mouth and then the granular jelly beverage for medication, instead of water, is put in the mouth. Thereafter, the drug and granular jelly beverage for medication may be allowed to flow down to the throat to be swallowed. Also, the drug may be put in the granular jelly beverage for medication, which is placed in advance in a container such as a cup, and mixed. Thereafter, this mixture may be swallowed.

EXAMPLES

The present invention will be described in more detail by way of Examples and Comparative Example below, but the present invention is by no means limited to these Examples.

Example 1

According to the method for production shown in FIG. 1, sorbitol and dextran were added to water (50 parts) warmed to about 50° C. Soybean lecithin was further added thereto while keeping the water temperature at 50° C. and the mixture was then stirred. Subsequently, xanthane gum dissolved in water (20 parts) warmed in advance was gradually added, thereby obtaining a mixture. To this mixture, citric acid was added and stirred. A flavoring agent and water were further added thereto and the final total volume was adjusted. The resultant was filled in a container and allowed to cool, thereby obtaining a granular jelly beverage for medication. The blending percentage of each ingredient is shown in Table 1.

The pH of the granular jelly beverage for medication was 4.2. The jelly strength thereof was 40.0 g/cm². The maximum length of granular jelly was 5.0 mm. The water reduction rate was 0.5%.

The jelly strength was measured by the method described later.

TABLE 1

| Example 1 | Mass % |
| --- | --- |
| Sorbitol (b: bitterness masking auxiliary ingredient) | 15.0 |
| Dextran (c-1: gelling ingredient) | 1.0 |
| Xanthane gum (c: aggregation-inhibiting gelling ingredient) | 0.2 |
| Citric acid (d: taste adjusting ingredient) | 0.5 |

TABLE 1-continued

| Example 1 | Mass % |
| --- | --- |
| Soybean lecithin (a: bitterness masking ingredient) | 0.2 |
| Flavoring agent | 0.1 |
| Purified water (e: water) | 83.0 |
| Total amount | 100.0 |

Example 2

According to the method for production shown in FIG. 2, erythritol and sorbitol were added to water (50 parts) warmed to about 50° C. Cacao fat and oil were further added thereto while keeping the water temperature at 50° C. and the mixture was then stirred, thereby obtaining a mixture (first mixture). Subsequently, agar, locust bean gum and sucrose fatty acid ester were added in water (20 parts) warmed in advance at about 50° C. and stirred to obtain a mixture. And then, this resulting mixture was gradually added to the first mixture and stirred, thereby obtaining the second mixture. Thereafter, to the second mixture, citric acid was added and stirred. A flavoring agent and water were further added thereto and the final total volume was adjusted. The resultant was filled in a container and allowed to cool, thereby obtaining a granular jelly beverage for medication. The blending percentage of each ingredient is shown in Table 2.

The pH of the granular jelly beverage for medication was 3.3. The jelly strength thereof was 45.5 g/cm². The maximum length of granular jelly was 5.0 mm. The water reduction rate was 2.0%.

TABLE 2

| Example 2 | Mass % |
| --- | --- |
| Erythritol (b: bitterness masking auxiliary ingredient) | 5.0 |
| Sorbitol (b: bitterness masking auxiliary ingredient) | 5.0 |
| Agar (c-1: gelling ingredient) | 0.1 |
| Locust bean gum (c: aggregation-inhibiting gelling ingredient) | 0.2 |
| Citric acid (d: taste adjusting ingredient) | 1.5 |
| Cacao fat and oil (a: bitterness masking ingredient) | 0.4 |
| Sucrose fatty acid ester (f: ingredient for inhibiting water repellency) | 0.1 |
| Flavoring agent | 0.2 |
| Purified water (e: water) | 87.5 |
| Total amount | 100.0 |

Comparative Example

Erythritol, hydrogenated maltose starch syrup, locust bean gum, xanthane gum, carrageenan and calcium lactate were added to water (50 parts) warmed to about 50° C. A homogenized sucrose fatty acid ester and cacao fat and oil were added thereto while keeping the water temperature at 50° C. and the mixture was then stirred. A flavoring agent, sweetener and water were further added thereto and the final total volume was adjusted. The resultant was filled in a container and allowed to cool, thereby obtaining a bitterness masking granular jelly without a taste adjusting ingredient. The blending percentage of each ingredient is shown in Table 3.

The pH of the bitterness masking granular jelly beverage was 6.6. The jelly strength thereof was 39.8 g/cm². The maximum length of granular jelly was 5.0 mm. The water reduction rate was 1.8%.

TABLE 3

| Comparative example | Mass % |
| --- | --- |
| Erythritol | 10.0 |
| Hydrogenated maltose starch syrup | 4.0 |
| Locust bean gum | 0.1 |
| Xanthane gum | 0.05 |
| Carrageenan | 0.2 |
| Calcium lactate | 0.1 |
| Cacao fat and oil | 0.8 |
| Flavoring agent | 0.2 |
| Stevia | 0.05 |
| Sucrose fatty acid ester | 0.02 |
| Purified water | 84.48 |
| Total amount | 100.0 |

Reference Example

According to the method for production shown in FIG. 1, erythritol, xylitol and agar were added to water (50 parts) warmed to about 50° C. Soybean lecithin was further added thereto while keeping the water temperature at 50° C. and the mixture was then stirred. Subsequently, sucrose fatty acid ester was gradually added to water (20 parts) warmed in advance and stirred, thereby obtaining a mixture. When citric acid was added to this mixture, lumps were formed. Although the mixture was stirred, the lumps were not able to be dissolved. Thus, due to lack of an aggregation-inhibiting gelling ingredient, aggregation occurred and an appropriate gel was not able to be formed in this example. The blending percentage of each ingredient in this example is shown in Table 4.

TABLE 4

| Reference example | Mass % |
| --- | --- |
| Erythritol | 5.0 |
| Xylitol | 5.0 |
| Agar | 0.2 |
| Citric acid | 1.5 |
| Soybean lecithin | 0.2 |
| Sucrose fatty acid ester | 0.01 |
| Purified water | 88.09 |
| Total amount | 100.0 |

[Determination of Jelly Strength]
Measuring apparatus: rheometer (manufactured by Rheotech, Type: RT-2020J)
Plunger: 1 cm$\phi$
Compression rate: 2 cm/min
Measurement Method:

After left to stand at 20° C. for not less than 15 hours, a sample was taken out such that a jelly was not broken. The sample was carefully taken out with an appropriate container (3 cm$\phi$×2 cm) so as not to be broken. The strength of the sample was measured using the above-mentioned measuring apparatus and the jelly strength was calculated according to the following formula (1):

Jelly strength (g/cm$^2$)=Measured strength(g)/0.785 (cm$^2$)  (1)

Here, 0.785 cm$^2$ is the surface area of the plunger.
[Performance Evaluation]

The granular jelly beverage of each example was subjected to the following sensory evaluation by human subjects. The obtained results are shown in Tables 4 to 10.

(Conditions for Sensory Evaluation)

As shown below, a prescribed amount of a drug to be evaluated, which drug was prescribed in the basis of herbal remedy, was treated with a prescribed amount of the granular jelly beverage of each example. The obtained sample (granular jelly beverage containing herbal medicine) was taken by six test subjects (healthy adults; five males and one female) and evaluated for each of the tastes at a prescribed time as described below.

In regard to a sweet taste, the cases where it was not different from that of a herbal medicine alone was indicated as "III", the cases where it was slightly stronger than that of the herbal medicine itself was indicated as "II", and the cases where it was stronger than that of the herbal medicine itself was indicated as "I".

In regard to a bitter taste, the cases where it was not different from that of a herbal medicine itself was indicated as "III", the cases where it was slightly weaker than that of the herbal medicine itself was indicated as "II", and the cases it where the bitter taste was not perceived was indicated as "I".

In regard to a sour taste, the cases where it was weaker than that of a herbal medicine itself was indicated as "IV", the cases where it was not different from that of the herbal medicine itself was indicated as "III", the cases where it was slightly stronger than that of the herbal medicine itself was indicated as "II", and in the cases where it was stronger than that of the herbal medicine itself was indicated as "I".

In regard to a pungent taste, the cases where it was not different from that of a herbal medicine itself was indicated as "III", the cases where it was slightly weaker than that of the herbal medicine itself was indicated as "II", and the cases it where the pungent taste was not perceived was indicated as "I".

In regard to an unpleasant smell, the cases where an unpleasant smell of a herbal medicine existed was indicated as "III", the cases where the unpleasant smell of the herbal medicine slightly existed was indicated as "II", and the cases it where no unpleasant smells of the herbal medicine existed was indicated as "I".

In regard to a smell of flavoring agent, the cases where the smell of flavoring agent existed was indicated as "III", the cases where the smell of flavoring agent slightly existed was indicated as "II", and the cases where no smells of flavoring agent existed was indicated as "I".

(1) Drugs to be Evaluated
 (i) Orengedokuto Extract Granules (manufactured by Tsumura & Co., No. 15)
 (ii) Shofusan Extract Granules (manufactured by Tsumura & Co., No. 22)
 (iii) Goshuyuto Extract Granules (manufactured by Tsumura & Co., No. 31)
 (iv) Unseiin Extract Granules (manufactured by Tsumura & Co., No. 57)
 (v) Jizusoippo Extract Granules (manufactured by Tsumura & Co., No. 59)
 (vi) Saikoseikanto Extract Granules (manufactured by Tsumura & Co., No. 80)
 (vii) Saireito Extract Granules (manufactured by Tsumura & Co. No. 114)
(2) Amount of Drugs
 The amount of each drug was 1.25 g.
(3) Preparation of Samples
 To the granular jelly beverage (10 g), the drug (1.25 g) was added and stirred well.

The test subject put the jelly mixed with the drug and stirred well in her/his mouth and, 10 seconds later, took it out. And, 5 seconds later, they conducted evaluation.

TABLE 5

| Orengedokuto Extract Granules | | Comparative Example | Example 1 | Example 2 |
|---|---|---|---|---|
| Sweet taste | Absent | II | II | II |
| Bitter taste | Present | II | II | I |
| Sour taste | Absent | III | II | II |
| Pungent taste | Absent | III | III | III |
| Herbal odor (Smells of herbs) | — | II | I | I |
| Jelly flavor (Flavoring strength) | — | II | II | III |

TABLE 6

| Shofusan Extract Granules | | Comparative Example | Example 1 | Example 2 |
|---|---|---|---|---|
| Sweet taste | Slightly present | II | II | II |
| Bitter taste | Present | II | II | I |
| Sour taste | Absent | III | III | II |
| Pungent taste | Absent | III | III | III |
| Herbal odor (Smells of herbs) | — | II | I | I |
| Jelly flavor (Flavoring strength) | — | II | II | III |

TABLE 7

| Goshuyuto Extract Granules | | Comparative Example | Example 1 | Example 2 |
|---|---|---|---|---|
| Sweet taste | Absent | II | II | II |
| Bitter taste | Slightly Present | III | I | I |
| Sour taste | Absent | III | II | II |
| Pungent taste | Present | II | I | I |
| Herbal odor (Smells of herbs) | — | II | I | I |
| Jelly flavor (Flavoring strength) | — | II | II | III |

TABLE 8

| Unseiin Extract Granules | | Comparative Example | Example 1 | Example 2 |
|---|---|---|---|---|
| Sweet taste | Absent | II | I | I |
| Bitter taste | Present | II | II | II |
| Sour taste | Absent | III | II | II |
| Pungent taste | Absent | III | III | III |
| Herbal odor (Smells of herbs) | — | II | I | II |
| Jelly flavor (Flavoring strength) | — | II | III | II |

TABLE 9

| Jizusoippo Extract Granules | | Comparative Example | Example 1 | Example 2 |
|---|---|---|---|---|
| Sweet taste | Slightly present | II | II | II |
| Bitter taste | Slightly present | I | I | I |
| Sour taste | Absent | III | II | II |
| Pungent taste | Absent | III | III | III |
| Herbal odor (Smells of herbs) | — | II | I | I |
| Jelly flavor (Flavoring strength) | — | II | II | III |

TABLE 10

| Saikoseikanto Extract Granules | | Comparative Example | Example 1 | Example 2 |
|---|---|---|---|---|
| Sweet taste | Absent | II | II | II |
| Bitter taste | Present | II | II | II |
| Sour taste | Absent | III | II | II |
| Pungent taste | Absent | III | III | III |
| Herbal odor (Smells of herbs) | — | II | I | II |
| Jelly flavor (Flavoring strength) | — | II | II | II |

TABLE 11

| Saireito Extract Granules | | Comparative Example | Example 1 | Example 2 |
|---|---|---|---|---|
| Sweet taste | Absent | II | II | II |
| Bitter taste | Slightly Present | II | II | I |
| Sour taste | Slightly Present | IV | III | III |
| Pungent taste | Slightly Present | I | I | I |
| Herbal odor (Smells of herbs) | — | I | I | I |
| Jelly flavor (Flavoring strength) | — | II | II | III |

[Discussion on Performance Evaluation]

As shown in Tables 5 to 11, when the granular jelly beverages for medication of Examples 1 and 2 were taken in conjunction with the herbal medicine (i) to (vii), there was a tendency that the sweet taste and sour taste became stronger. Because of this tendency, even if the bitter taste existed, it was different from a bitter taste which makes the herbal medicine difficult to be swallowed. Rather, there was a tendency that the bitter taste and pungent taste were weakened and the herbal medicine was more easily taken. In addition, it was able to be confirmed that, by using the granular jelly beverages for medication of these Examples, the drug was more easily swallowed with no unpleasant smells of herbs existing and tastes being improved.

On the other hand, in the Comparative Example (conventional bitterness masking granular jelly beverage), the sour taste and pungent taste were not different from those of the herbal medicine itself and the smell of herbs remained. Thus, it was not suitable for taking the herbal medicine.

INDUSTRIAL APPLICABILITY

According to the present invention, by using the aggregation-inhibiting gelling ingredient in addition to the bitterness masking ingredient, the bitterness masking auxiliary ingredient and the taste adjusting ingredient, the granular jelly beverage for medication and the method for production thereof can be provided, which granular jelly beverage is able to, without impairing the pharmacological effects of a crude drug and/or herbal medicine, mask the bitterness of these drugs and coat the drugs for easier swallowing as well as to have an good taste even after mixed with the drug composed of crude drug and/or herbal medicine.

What is claimed is:

1. A granular jelly beverage for medication used for taking a crude drug(s) and/or herbal medicine(s), said granular jelly beverage for medication comprising:
   (a) 0.1 to 15.0% by mass of a bitterness masking ingredient comprising a plant fat and oil and/or animal fat and oil;
   (b) 5.0 to 20.0% by mass of a bitterness masking auxiliary ingredient comprising a sugar alcohol;
   (c) 0.1 to 5.0% by mass of at least one type of an aggregation-inhibiting gelling ingredient selected from the group consisting of carrageenan, gellan gum, locust bean gum, xanthan gum, guar gum, pectin, tapioca starch, and starch;
   (d) 0.1 to 5.0% by mass of at least one type of a taste adjusting ingredient selected from the group consisting of acids, derivatives thereof and salts thereof; and
   (e) a balance of water,
   wherein:
   the granular jelly beverage comprises components (a) to (d) in the form of a plurality of jelly granules;
   the granular jelly beverage has a pH of 2.5 to 5.0;
   the jelly granules have a maximum length of 1 to 10 mm; and
   the granular jelly beverage is packaged without the crude drug(s) and/or herbal medicine(s) such that the granular jelly beverage is adapted to be mixed by an end user with the crude drug(s) and/or herbal medicine(s).

2. The granular jelly beverage for medication according to claim 1, further comprising at least one type of a gelling ingredient (c-1) selected from the group consisting of agar, furcellaran, gelatin, curdlan, psyllium seed gum, alginic acid, alginate, mannan, tamarind gum, dextran, carboxymethyl cellulose, carboxymethyl cellulose sodium, and methylcellulose.

3. The granular jelly beverage for medication according to claim 2, wherein, in a total amount of said aggregation-inhibiting gelling ingredient (c) and said gelling ingredient (c-1), said aggregation-inhibiting gelling ingredient (c) is 5.0 to 95.0% by mass of such total.

4. The granular jelly beverage for medication according to claim 1, which has a pH of 2.7 to 4.5.

5. The granular jelly beverage for medication according to claim 1, further comprising 0.01 to 1.5% by mass of at least one type of an ingredient for inhibiting water repellency (f) selected from the group consisting of sucrose fatty acid esters, glycerine fatty acid esters, sorbitan fatty acid esters, propylene glycols and propylene glycol fatty acid esters.

6. The granular jelly beverage for medication according to claim 1, wherein the jelly granules have a jelly strength at 20° C. of 10 to 100 g/cm$^2$.

7. The granular jelly beverage for medication according to claim 1, wherein said plant fat and oil of said bitterness masking ingredient (a) is at least one selected from the group consisting of cacao fat and/or oil, lecithin, soybean oil, salad oil, edible safflower oil, sunflower oil, canola oil, corn oil, rice bran oil, peanut oil, olive oil, sesame oil, linseed oil, coconut oil, palm oil, mixed oil, margarine and shortening; and said animal fat and oil is at least one type selected from the group consisting of lard, unsalted butter, butter, cheese, cream, meat fats, and fish oils.

8. The granular jelly beverage for medication according to claim 1, wherein said sugar alcohol in said bitterness masking auxiliary ingredient (b) is at least one selected from the group consisting of hydrogenated maltose starch syrup, hydrogenated starch syrup, hydrogenated lactose, xylitol, erythritol, sorbitol and mannitol.

9. The granular jelly beverage for medication according to claim 1, wherein said taste adjusting ingredient (d) is at least one selected from the group consisting of adipic acid, L-ascorbic acid, L-asparatic acid, L-arginine, L-glutamic acid, citric acid, glucono delta lactone, gluconic acid, succinic acid, DL-tartaric acid, L-tartaric acid, lactic acid, fumaric acid, butyric acid, DL-malic acid, derivatives thereof and salts thereof.

10. The granular jelly beverage for medication according to claim 1, wherein said crude drug(s) and/or herbal medicine(s) are/is at least one of formulation selected from the group consisting of powders, granules, balls, capsules, powdered extract agents, tablets, extracts and syrups.

11. A method for producing said granular jelly beverage for medication according to claim 1, said method comprising mixing said bitterness masking ingredient (a), said bitterness masking auxiliary ingredient (b), said aggregation-inhibiting gelling ingredient (c) and at least a part of said water (e) to obtain a mixture; and thereafter mixing said taste adjusting ingredient (d) into said mixture.

* * * * *